United States Patent [19]

Schäfer et al.

[11] Patent Number: 5,143,694
[45] Date of Patent: Sep. 1, 1992

[54] TEST STRIP EVALUATING INSTRUMENT FOR MULTIPLE TEST STRIPS

[75] Inventors: Dieter Schäfer, Schriesheim; Stephan Sattler, Peissenberg; Peter Scheunert, Mannheim; Franz Laufenberg, Grünstadt; Hans List, Lampenhain; Klaus Steeg, Kronau; Eugen Serrallach, Edingen, all of Fed. Rep. of Germany

[73] Assignee: Boehringer Mannheim GmbH, Mannheim, Fed. Rep. of Germany

[21] Appl. No.: 622,053

[22] Filed: Dec. 4, 1990

[30] Foreign Application Priority Data

Dec. 5, 1989 [DE] Fed. Rep. of Germany ....... 3940152

[51] Int. Cl.$^5$ ...................... G01N 21/13; G01N 35/04
[52] U.S. Cl. ......................................... 422/65; 422/63; 422/66; 436/43; 436/46; 436/47; 436/44
[58] Field of Search ....................... 422/65, 61, 63, 58, 422/66; 436/47, 48, 46, 43, 44

[56] References Cited

U.S. PATENT DOCUMENTS

| | | | |
|---|---|---|---|
| 3,645,690 | 2/1972 | Rochte et al. | 436/48 |
| 4,689,202 | 8/1987 | Khoja et al. | 436/47 |
| 4,796,197 | 1/1989 | Lissot et al. | 436/47 |
| 4,826,659 | 5/1989 | Akisada | 422/63 |
| 4,928,540 | 5/1990 | Kido et al. | 422/63 |
| 5,039,615 | 8/1991 | Takahata | 422/63 |

Primary Examiner—James C. Housel
Assistant Examiner—Long V. Le
Attorney, Agent, or Firm—Nikaido, Marmelstein, Murray & Oram

[57] ABSTRACT

A test strip evaluating instrument is used for testing of multiple test strips, and has a transport and positioning device which transports the test strips at right angles to their longitudinal direction from a test strip feed area along a transport path to a disposal area. At least one measuring station with an optical measuring unit is arranged on the transport path. Rails, on which the test strips slide, run along the transport path. The test strips are transported in a step-wise manner by at least two rows of cam elements following one another in the transport direction, and these two rows of cam elements move synchronously with one another in a periodically recurring movement path. The handling of the test strips is facilitated without impairment of the measuring accuracy by the fact that the rails are longitudinally aligned as thin ribs in a disposable transport insert made of a thin plastic material, in which the cam elements engage from above between adjacent pairs of the rails of the transport insert, and in which a bearing element is provided for the tranport insert which supports the transport insert with a support surface in a central area lying between the test strip feed area and the disposal area. A rigid contact-pressure element is also provided, against which the test strip is pressed elastically from below during the measurement, and this contact-pressure element is disposed at the measuring station at a predetermined distance from the optical measuring unit.

13 Claims, 4 Drawing Sheets

TEST STRIP EVALUATING INSTRUMENT FOR MULTIPLE TEST STRIPS

BACKGROUND OF THE INVENTION relates to a test strip evaluating instrument for multiple test strips with a transport and positioning device by means of which the test strips are transported at right angles to their longitudinal direction from a test strip feed area along a transport path to a disposal area, in which at least one measuring station with an optical measuring unit is arranged on the transport path, rails on which the test strips slide running along the transport path, and at least two rows of cam elements following one another in the transport direction, the cam elements being driven synchronously with one another in a periodically recurring movement path such that they transport the test strips in a step-wise manner.

Multiple test strips are in common use for the analysis of materials to be tested, for example for the analysis of urine. These types of test strips have a plurality of adjacent, equally spaced test fields, which contain reagents in different combinations for determining various components of the sample. The test strips are usually dipped briefly into the material to be tested, e.g. urine. The reaction of the sample with the reagent leads to an optically detectable change, usually a color change, on the test fields. This change is evaluated visually or with a suitable evaluating instrument. Instruments for the evaluation of test strips are matched as regards their properties with the test strips of a particular manufacturer. The type of test strips used and a compatible evaluating instrument together can be considered to form a test strip analysis system.

High demands are made of test strip evaluating instruments. The evaluation of the optically detectable change on the test fields usually takes place by reflection photometry. The accuracy of the measurement is here largely dependent on the exact positioning of the test strips in relation to the optical measuring unit. Since there is a trend towards smaller and smaller test fields and only the central area of each test strip can be used for an accurate measurement, high demands have to be imposed on the positioning of the test strip with respect to the test field area. This involves the longitudinal and transverse positioning of the test strip. Particular importance attaches to the precise maintenance of the distance between the optical measuring unit and the test field surface (i.e., distance positioning), because the accuracy of the optical measurement depends on this distance to a very great extent.

A test strip evaluating instrument of the kind described in the preamble is known from EP-A-174 564 which corresponds to U.S. Pat. No. 4,689,202. The rails of this reference are part of a so-called base tray and run, interrupted by two reading station platforms, between a first depression in the sample feed area and a second depression in the disposal area.

The base tray comprises two longitudinal slots through which pegs serving as cam elements can penetrate from below the base tra up to and above the rails. The pegs are part of a test strip conveying element which follows a particular path, namely a closed curve in a vertical plane (vertical orbital path). This curve contains a horizontal path section, in which the pegs are situated in their topmost position and transport the test strips, and a roughly semi-circular-shaped path section in which the pegs, after completion of a transport step, are withdrawn downwards, run back and are raised again so that tiles project from below the base tray so as to extend above the rails behind the next test strip to be conveyed.

The accuracy of distance positioning is ensured in the case of the above-described previously known instrument by the fact that the test strips rest on the measurement platforms during the measurement and are pressed elastically against the latter from above. Particular importance is attached to the fact that the platforms have a plane surface at least in the region of the test fields. In addition the base tray has to be of stable overall design and be exactly positioned, in order to reasure the measuring accuracy.

The known device meets the requirements as to accuracy of the measurement. The design is, however, relatively complicated. Moreover, several parts of the instrument are contaminated by the material being tested, such as urine, during use. This applies particularly to the base tray and the test strip conveying element. In order to prevent the material being tested, particularly urine, from penetrating into the inside of the unit, both the base tray and the test strip conveying element have raised edges around their respective circumferences. Although the material being tested, e.g. urine, is thereby contained, it nevertheless collects on the planar surfaces of these elements. These surface therefore have to be cleaned thoroughly at regular intervals.

Transport of analysis elements by means of vertically mobile rails and horizontal transport elements is known from U.S. Pat. No. 3,645,690. The basic transport principle shown in this reference. is also described as a "walking beam". The conveyor shown in this reference, having horizontally mobile transport elements, is located beneath the analysis elements. Furthermore, in this reference, no transport insert is provided, and the analysis elements described therein are not test strips of the type tested in the present invention. According to this reference, the analytical evaluation in that system takes place by transmission photometry, and accordingly the special requirements regarding positioning accuracy which are associated with reflection-photometric evaluation (as used in the present invention) do not therefore arise with the known apparatus shown in this reference.

SUMMARY OF THE INVENTION

It is an object of the invention to provide a test strip evaluating instrument in which easier handling of test strips is achieved without impairment of the measuring accuracy of the test strip evaluating instrument. In particular, it is an object of the instrument according to the present invention to effect a reduction in the effort required to keep the instrument clean as compared with prior devices of the type described above.

These objects are achieved with an instrument of the kind having a transport and positioning device by mean of which the test strips are transported at right angles to their longitudina direction from a test strip feed area along a transport path to a disposal area, in which at least one measuring station with an optical measuring unit is arranged on the transport path, rails on which the test strips slide running along the transport path, and at least two rows of cam elements following one another in the transport direction, the cam elements being driven synchronously with one another in a periodically recurring movement path in such a way that they transport the test strips in a step-wise manner, in that the fact that the rails extend longitudinally in a disposable transport insert made of a thin plastics material, the cam elements engage between the rails of the transport insert, a bearing element is provided for the transport insert which supports the transport insert with a support surface in a central area lying between the test strip feed area and the disposal area, and a rigid contact-pressure element, against which the test strip is pressed elastically from below during the measurement, is provided at the measuring station at a defined distance from the optical measuring unit.

The transport insert according to the present invention i disposable, i.e. it is a throw-away part for one time only use. It can be manufactured at low cost—preferably by a known type of deep-drawing method—from a thermoplastic plastics material, in particular polystyrene, polypropylene or polyvinylchloride, and covers the entire transport path of the test strips from the test strip feed area to a disposal area. Contamination of th unit e by the substance being tested, e.g. urine, is thus prevented to a very large extent.

Because the rigid contact-pressure element above the transport track at the measuring station is provided at a defined distance from the measuring unit, extremely accurate distance positioning is ensured. The rails themselves are part of a throw-away component made of thin plastic material of preferably less than 0.5 mm thickness. During the pressing of the test strips against the rigid contact-pressure element, a certain elasticity of the pressing component is required. It is preferable for the transport insert to have a profile which is substantially continuous between the test strip feed area and the disposal area, so that the rails, in contrast to the above-mentioned previously known instrument, also run continuously past the measuring station. The shape of the profile is moreover preferably selected so that the transport insert is elastically deformable in the region of the measuring station in a direction which is normal to the transport path. The support surface of the bearing element is substantially planar in the region of the measuring station. The elasticity required during the pressing against the rigid contact-pressure element is ensured by the construction of the transport insert.

The invention will be described in greater detail below with reference to an embodiment which is illustrated in the drawings.

DETAILED DESCRIPTION OF THE PREFERRED EMBODIMENT

Figure 1:
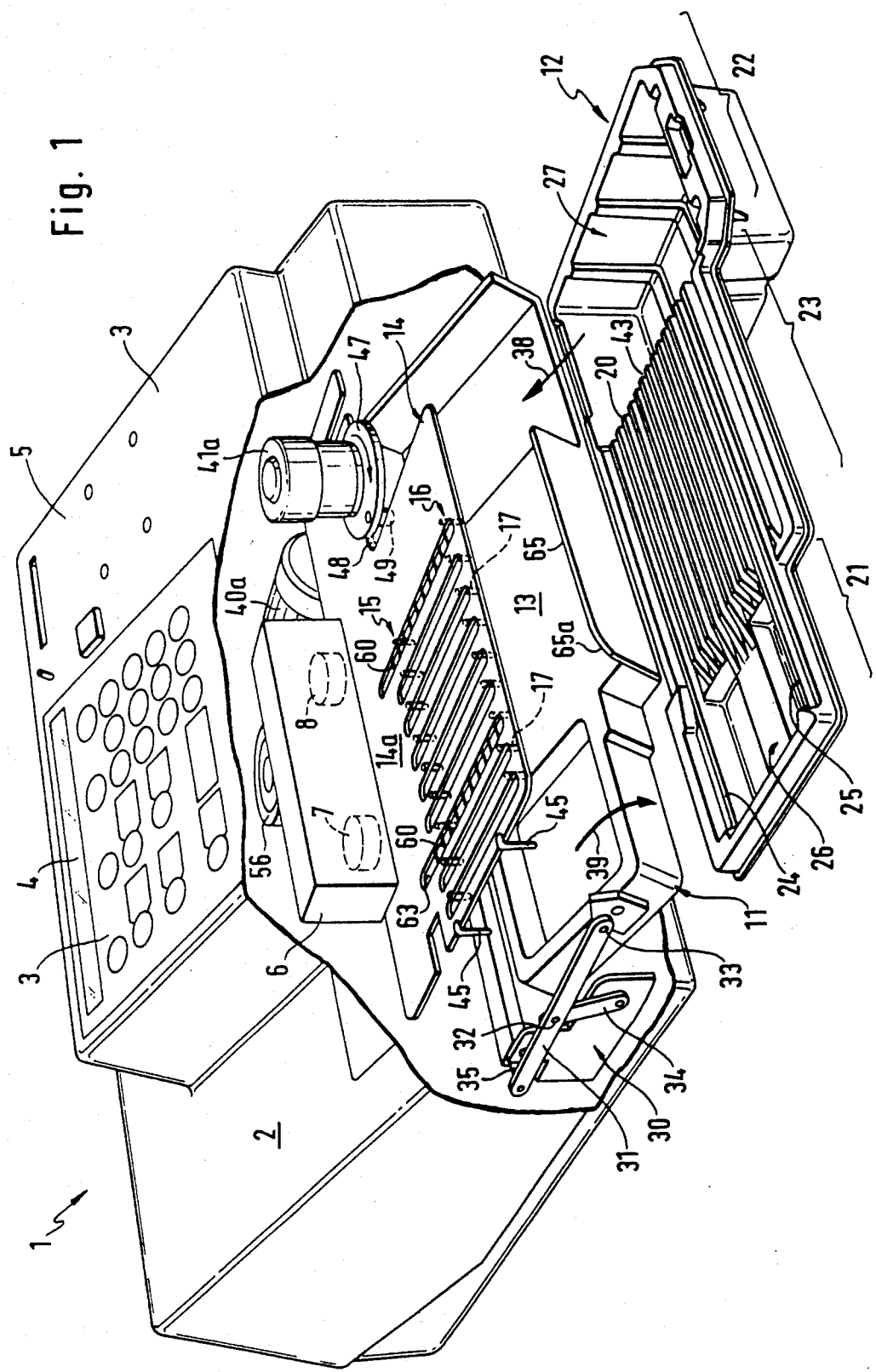
FIG. 1 illustrates a test strip evaluating instrument according to the present invention in a perspective view, partially broken away in section, with a transport insert removed.
Figure 2:
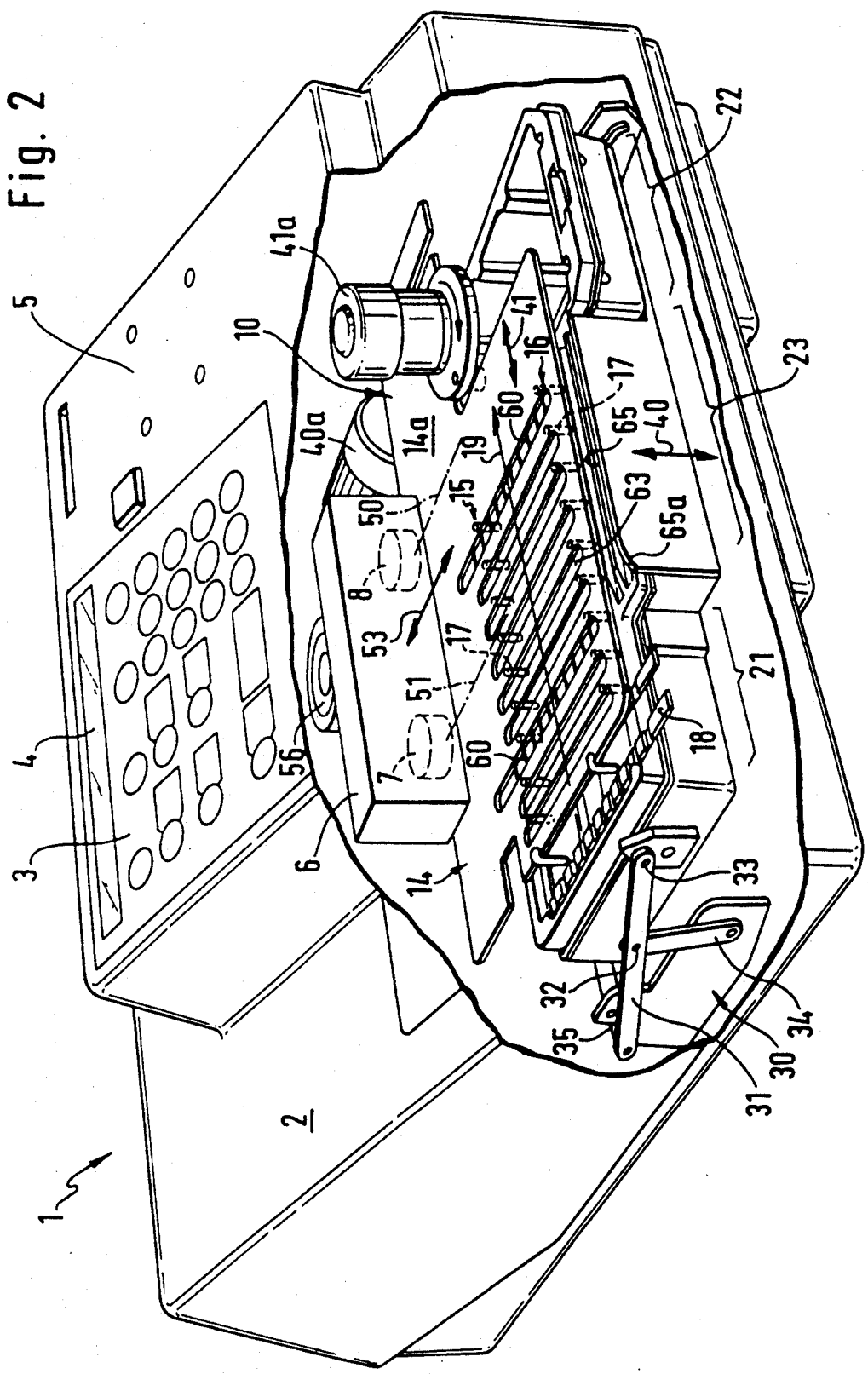
FIG. 2 is a perspective view of a test strip evaluating instrument similar to that shown in FIG. 1, but with the transport insert in an operational position.

A test strip evaluating instrument 1 is shown in FIGS. 1 and 2, and has a casing 2 with an operator panel 3, a display 4, and a printer 5. A measuring device with a measuring head 6 comprises two optical measuring units 7 and 8 and associated measurement electronics (not illustrated). These components can be of conventional design. They are not therefore described in detail herein.

The present invention relates primarily to features which make possible the automatic feeding of the test strips 18 to at least one measuring station, their precise positioning at the measuring station, and their disposal These features are concealed during operation of the instrument 1 by the casing 2, which is partially cut away in the drawings to show internal structure of the instrument 1.

A transport and positioning device 10 incorporates a bearing element 11 with a support surface 13, a transport insert 12, and a test strip conveyor 14 with two rows 15, 16 of peg-shaped cam elements 17.

Test strips 18 are transported as shown in FIG. 2, at right angles to their longitudinal direction along a transport path 19 on rails 20 from a test strip feed area 21 to a test strip disposal area 22. The rails 20 are formed as longitudinally extending raised ribs in the transport insert 12. In the preferred embodiment shown in the drawings, some of the rails of the transport insert 12, namely rails 24 and 25, extend along the entire test strip feed area 21 as well as a central area 23. The central area 23 lies between the test strip feed are 21 and the disposal area 22. The remaining rails 20 extend only along the central area 23.

In the test strip feed area 21 and in the disposal area 22 the transport insert 12 includes trough-shaped depressions 26 and 27 which open upwardly. The trough 26 collects dripping excess sample liquid. The trough 27 is large enough to collect the test strip 18 usually evaluated in one operating cycle, for example one hundred test strips 18.

The transport insert 12 can easilY be positioned on the bearing element 11 and removed therefrom. To this end it is useful if the bearing element 11 can be moved downwardly away from the test strip conveyor 14. The test strip conveyor 14 has a transport plate 14a as shown in FIG. 1. It is particularly preferable for the bearing element 11 to be tiltable forwardly at the same time as it is movable downwardly, as shown in FIG. 1. In the represented embodiment of the invention, the foregoing arrangement is achieved by a multi-link mechanism 30. The multi-link mechanism 30 includes a supporting beam 31, two bearing-element-side bearings 32 and 33, an arm 34, and a rear pivoted lever 35. Other devices for moving the bearing element 11 downwardly and away from the test strip conveyor 14, such as by means of servo-motors, tooth-wheel gears and the like.

When the bearing element 11 is pivoted downwardly and forwardly away from the test strip conveyor 14 and hence from the cam elements 17, the transport insert 12 can easily be inserted into the bearing element 11 in the direction indicated by the arrow 38. The bearing element 11 is shaped in such a way that the transport insert 12 forms a locking fit thereon when the transport insert 12 is in a specified position relative to the bearing element 11, as can be seen in FIGS. 1 and 2. Conversely the transport insert 12 can, as indicated by the arrow 39, be just as easily removed from the bearing element 11. The transport insert 12 can thereafter be disposed of, together with any used test strips 18 which are contained in the trough 27.

The transport of the test strips 18 from the test strip feed area 21 to the disposal area 22 is brought about according to the preferred embodiment by the periodic up-and-down movement of the bearing element 11 and hence the transport insert 12, indicated by arrow 40 in FIG. 2, the movement being in a direction which is normal to the transport path. During this time, the cam elements 17 move periodically in a to-and-fro movement, in a direction which is indicated by arrow 41 in FIG. 2, this direction being parallel to the transport path 20. Both movements are coupled such that the test strips 18 are transported in a step-wise manner from the test strip feed area 21 to the disposal area 22, as will be explained in further detail below.

Figure 3:
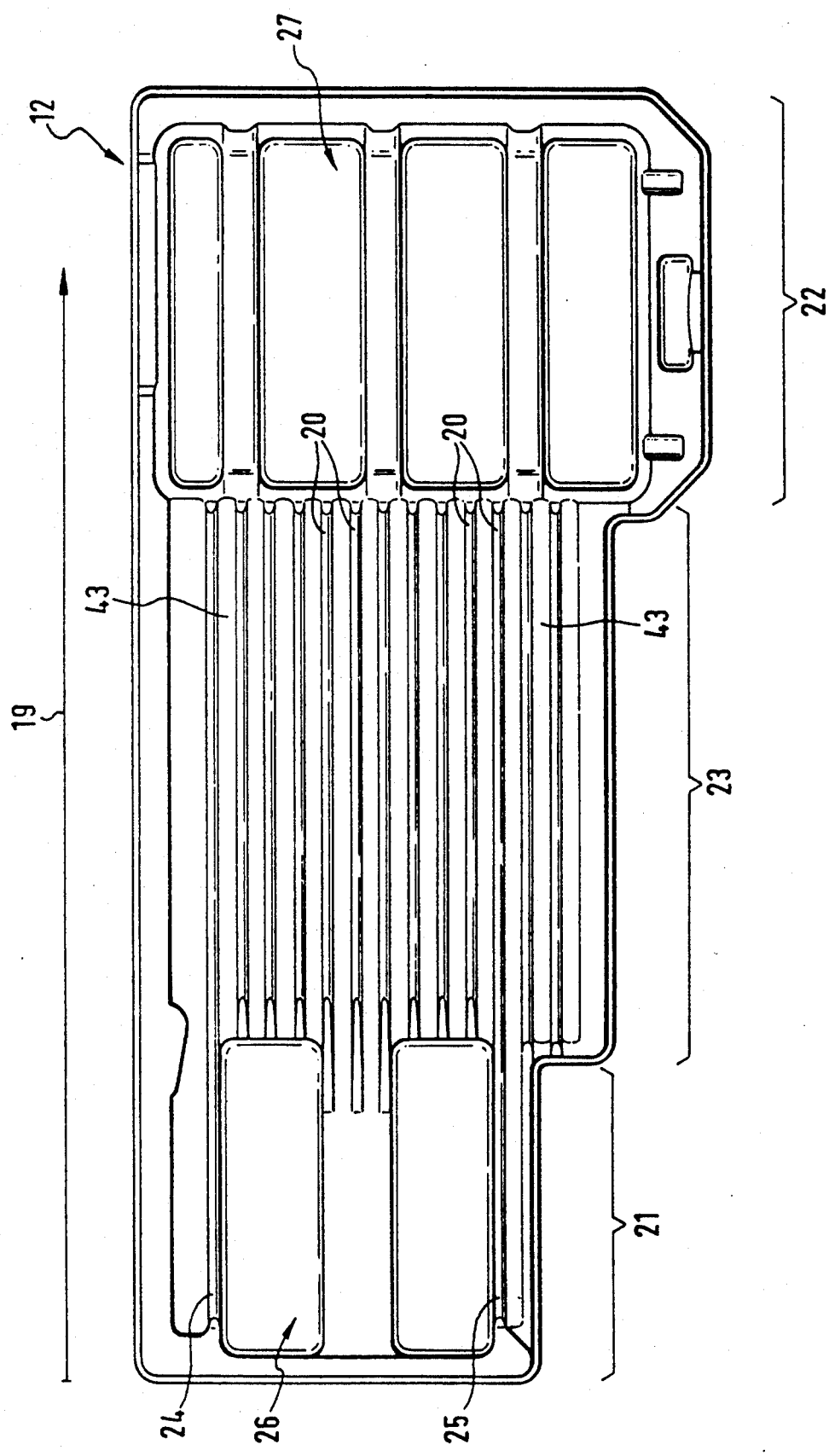
FIG. 3 is a top elevational view of the transport insert according to the present invention.

A transport cycle takes place in the simplest case as follows: On the raising of the bearing element 11 and hence of the transport insert 12, the cam elements 17 penetrate into respective gaps 43 which exist between adjacent pairs of the rails 20. The test strip conveyor 14 is then moved, together with the cam elements 17, in the transport direction (to the right in FIGS. 1 to 3, and parallel to the direction indicated by the double-headed arrow 41 of FIG. 2). All the test strips 18 are thereby transported to the right by one step, each step being defined as the distance between leading edges of adjacent pairs of the cam elements 17 in the above-described transport direction. However, the steps can have a different length, which should preferably then be an integer multiple of the distance between leading edges of adjacent pairs of the cam elements 17.

Next, the bearing element 11 is lowered downwardly until the test strips 18 resting on the rails 20 are located beneath the cam elements 17. The test strip conveyor 14 is then moved in the opposite direction to the above-mentioned transport direction (i.e., the test strip conveyor is moved to the left in FIGS. 1 and 2). The travel distance of the test strip conveyor during the horizontal movement is slightly more than the test strip spacing in the central area 23. On the renewed raising of the bearing element 11, the cam elements 17 again mesh with the gaps 43. The transport cycle then can start afresh.

In one embodiment, the test strip conveyor 14 is not only used in the central area 23 of the transport path 20 a described for the transport of the test strips 18, but also serves at the same time for the uniform and parallel alignment of test strips 18 fed into the test strip feed area 21. This is achieved by the fact that alignment elements 45, which extend downwardly further than do the cam elements 17, are provided to the left of the rows 15 and 16 of the cam elements 17. The bearing element 11 with the transport insert 12 is, in this embodiment, first raised only up to an intermediate position in which the longer alignment elements 45 already terminate below the rails 24, 25 and hence impinge into the transport path of the test strips 18, while the shorter cam elements 17 are still located above test strips 18 located on the rails 20. The overall travel distance of the horizontal movement of the test strip conveyor 14 in the transport direction (arrow 41 to the right) is in this case considerably longer (at least twice as long) as the test strip spacing in a tile central area 23. In a first part of the horizontal movement, while the bearing element 11 is in the above-mentioned intermediate position, a test strip fed anywhere in the test strip feed area 21 is aligned. The bearing element 11 with the transport insert 12 is then raised so that the cam elements 17 also engage with the gaps 43 between the rails 20 and hence with the transport path of the test strips 18. In the subsequent second part of the horizontal movement of the test strip conveyor 14 in the transport direction, the alignment elements 45 act as normal cam elements. The remainder of the transport cycle takes place as described above, with the bearing element 11 with the transport insert 12 being lowered during th return of the conveyor 14 until the alignment elements 45 are also no longer located in the transport path of the test strips 18.

The described movement of the bearing element 11 and the test strip conveyor 14 can be realized in any of various ways which would be known to any one having skill in the art to which this aspect of the invention pertains. In the present invention, motors 40a and 41a, which drive the above-described movement of the bearing element 11, are represented in FIGS. 1 and 2. The transfer of the rotational movement of the motors 40a, 41a into the corresponding longitudinal movement of the above-mentioned moving components can, for example, take place by means of a transport disc 47, which carries a cam 49 for engagement with a connecting member 48 of the test strip conveyor 14. The components mentioned are for example guided on their movement path by means of sliding guides, which have been omitted for the sake of clarity in FIGS. 1 and 2.

Figure 4:
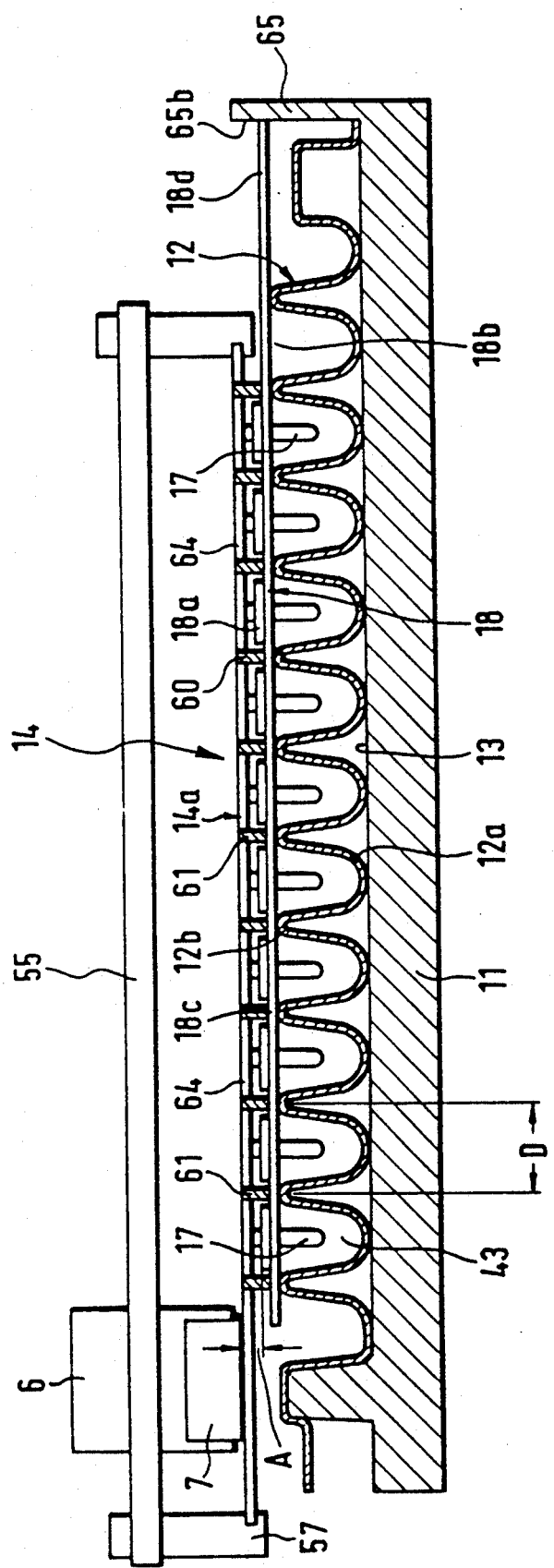
FIG. 4 shows a cross-section through a transport path of the test strip evaluating instrument according to the present invention, in a region of a measuring station.

The longitudinal positioning of the test strips 18 is brought about according to the preferred embodiment by a lateral guide wall 65, which is attached to the bearing element 11. The lateral guide wall 65 includes a front portion 65a as shown in FIG. 2 which extends parallel to the transport path 19 and an inside portion 65b which is shown in FIG. 4. The ends 18d of the test strips 18, during their transport, butt against the inside portion 65b of the lateral guide wall 65, the test strip 18 being thereby moved into a predetermined longitudinal position.

Reflection-photometric evaluation of the color change on the test fields is carried out by the optical measuring units 7 and 8, which are arranged at measuring stations 50 and 51 above the transport path 19 in the central area 23. In the case shown, the measuring units 7 and 8 are incorporated in a common measuring head 6, which is movable in the direction indicated by the arrow 53, at right angles to the transport path 19 over the test strips 18. In this way, all of the test fields 18a can be examined consecutively with one of the measuring units 7 and 8 per measuring station 50 and 51, respectively.

Alternatively, however, as is the case with certain known types of testing units, each measuring unit could be fitted with a plurality of optical systems arranged side by side, which examine the individual test fields.

FIG. 4 is a sectional view through the measuring station 50. The measuring head 6 with the optical measuring unit 7 is guided on a guide rail 55 (not shown in FIGS. 1 and 2). The drive is provided by a motor 56 (FIGS. 1 and 2), and the forces can be transmitted for example by a toothed belt drive (also not represented in the drawings).

To ensure accuracy of the resulting measurements, it is, as indicated above, of importance that a distance A shown in FIG. 4 between the optical measuring unit 7 and the test fields 18a on the test strip 18 be exactly defined and that it be the same for each of the test strips 18. This is achieved according to the invention, as mentioned, by the fact that at the measuring station the test strips 18 are urged elastically by their respective undersides 18b against a rigid contact-pressure element 60, which is located at a specified distance from the respective one of the optical measuring units 7 or 8.

In the preferred embodiment, the contact-pressure element 60 is ladder-shaped, and has a plurality of pegs 61 extending in the transport direction 19. The contact-pressure element 60 is provided on the test strip conveyor 14, and the pegs 61 are arranged such that, on pressing thereof against the test strip 18, the pegs 61 lie between ones of the test fields 18a. The pegs 61 are arranged, as can be seen from FIGS. 1 and 2, at right angles to and crossing the slots 63 which are provided in the transport plate 14a, these pegs 61 separating the slots 63 into a plurality of rectangular windows 64, through which the optical measurement takes place. The defined distance between the optical measuring unit 7 and the contact pressure element 60 is ensured by the fact that the transport plate 14a and the guide rail 55 are fixed to a common frame 57.

The test strips 18 are pressed elastically against the rigid contact-pressure elements 60. It is preferable for the transport insert 12 to be so formed in the area of the measuring stations and 51 that the insert 12 is elastically deformable in a direction normal to the transport path 19 and to the plane of the transport plate 14a (i.e. in the direction against an underside 18b of the test strips). This can be achieved in particular by formation of the rails 20 as shown in FIG. 4, such that they are continuous and undulating in form. It is also particularly advantageous if rounded portions 12a on the underside of the transport insert 12 are rounded less sharply than rounded portions 12b on the top side of the transport insert 12, on which the test strips 18 slide.

The material thickness of the transport insert is also of importance in this connection. The thickness of the material forming the transport insert 12 should preferably be less than 0.5 mm, and in particular should preferably lie between 0.15 and 0.3 mm. The support surface 13 of the bearing element 11, on which the transport insert 12 rests with its underside in the central area 23, is in this case generally planar, in order to support the transport insert 12 as uniformly as possible It is clear, however, that this planar support surface 13 need not be uninterrupted. In order to ensure uniform contact pressure over the whole length of the test strips 18, it is advantageous if the bearing element 11 is supported so as to be pivotable around an axis which is parallel to the transport path 19, as shown in FIGS. 1 and 2.

The distance D between the rails 20 is preferably a multiple of the test field spacing of the test strips 18. It is particularly preferable for the distance D between the rails 20 to be as large as the test field spacing. The test strips 18 are so guided on the transport path that—as represented in FIG. 4—sections 18c of the test strips 18 lie between the test fields and slide on the rails 20. Although the test strips 18 are in this case not supported at all below their respective test fields 18a, a highly precise distance positioning of the test strips 18 from the optical measuring units 7 and 8 can nevertheless be achieved. This arrangement of the rails 20 at the same time reduces so-called "carry-over" of the sample, i.e. the spreading of small amounts of sample over the rails 20 from one of the test strips 18 to another one of the test strips 18.

It will be understood that the above description of the present invention is susceptible to various modifications, changes and adaptations, and the same are intended to be comprehended within the meaning and range of equivalents of the appended claims.

What is claimed is:

1. A test strip evaluating instrument for conducting tests on a plurality of elongated test strips, said instrument comprising:
   a transport and positioning means for transporting the test strips in a direction at generally right angles to a longitudinal extent of the test strips, from a test strip feed area along a transport path to a disposal area;
   at least one measuring station having an optical measuring means disposed along said transport path for optically testing said test strips;
   a disposable transport insert formed of a plastic material, said disposable transport insert completely covering a bottom portion of said transport path and having a plurality of spaced apart rails for slidably supporting the test strips, each of said plurality of rails extending in a direction which is generally parallel to a transport direction of said test strips and being formed as longitudinal ribs in said plastic material, wherein liquid from said test strips which contacts said disposable transport insert is prevented from contacting other areas of said instrument;
   at least two rows of cam elements, each of said two rows of cam elements being aligned in said transport direction and being driven synchronously with each other in a periodically recurring movement path such that said two rows transport the test strips in a step-wise manner along said plurality of rails, wherein said two rows of cam elements engage the test strips from above and extend downwardly between adjacent ones of said plurality of rails;
   a bearing means for supporting said transport insert, said bearing means having a support surface for supporting the transport insert in a central area of said transport insert which lies between said test strip feed area and said disposal area; and
   a rigid contact-pressure means, having an underside against which the test strip is pressed elastically during measurement, provided at said measuring station, said rigid contact-pressure means being located at a predetermined distance from said optical measuring unit.

2. A test strip evaluating instrument according to claim 1, wherein said transport insert is composed of a thermoplastic plastics material.

3. A test strip evaluating instrument according to claim 1, wherein the wall thickness of said transport insert is less than 0.5 mm.

4. A test strip evaluating instrument according to claim 1, wherein said rails are disposed along a portion of said transport path corresponding to said measuring station.

5. A test strip evaluating instrument according to claim 4, wherein said rails of said transport insert are shaped such that said transport insert is elastically deformable in the vicinity of said measuring station in a direction normal to said transport path, and said support surface of said bearing means is substantially planar in said vicinity of said measuring station 6. A test strip evaluating instrument according to claim 1, wherein said transport insert comprises a trough disposed in the vicinity of said test strip feed area and in the vicinity of said disposal area.

7. A test strip evaluating instrument according to claim 1, wherein the distance between said rails is a multiple of a test field spacing between adjacent test fields located on the test strips, and wherein the test strips are guided along said transport path such that sections of said test strips lying between said test fields slide on said rails.

8. A test strip evaluating instrument according to claim 1, wherein said contact-pressure means at said measuring station is fixed to a test strip conveyor to which said cam elements are also fixed.

9. A test strip evaluating instrument according to claim 7, wherein said contact-pressure means includes a plurality of to said transport direction, said plurality of pegs being arranged such that they lie between adjacent ones of the test fields of the test strip when pressing on said test strip.

10. A test strip evaluating instrument according to claim 1, further comprising means for moving said bearing means periodically in an up and down movement which is normal to said transport path, and means for moving said cam elements periodically in a to-and-fro movement which is parallel to said transport path, said up and down and to-and-fro movements being coordinated to cause transport of said test strips in said stepwise manner along said transport path.

11. A test strip evaluating instrument according to claim 1, further comprising a lateral guide element having a front portion for positioning of the test strips along a longitudinal direction, said front portion impinging obliquely onto said transport path, and wherein said front part is not part of said transport insert.

12. A test strip evaluating instrument according to claim 1, wherein said transport insert is composed of polystyrene.

13. A test strip evaluating instrument according to claim 1, wherein the wall thickness of said transport insert is between 0.15 mm and 0.3 mm.

* * * * *